(12) United States Patent
Evans et al.

(10) Patent No.: US 9,636,073 B2
(45) Date of Patent: May 2, 2017

(54) DUAL-MODALITY MAMMOGRAPHY (71) Applicant: CAPERAY MEDICAL (PTY) LTD, Cape Town (ZA)

(72) Inventors: Michael David Evans, Fish Hoek (ZA); Raphael V. Smith, Observatory (ZA); Christopher Leonard Vaughan, Newlands (ZA)

(73) Assignee: CAPERAY MEDICAL (PTY) LTD. (ZA)

( * ) Notice: Subject to any disclaimer, the term of this patent is extended or adjusted under 35 U.S.C. 154(b) by 363 days.

(21) Appl. No.: 14/136,775

(22) Filed: Dec. 20, 2013

(65) Prior Publication Data
US 2014/0180082 A1    Jun. 26, 2014

(30) Foreign Application Priority Data

Dec. 21, 2012   (ZA) .................................. 201209726
Jun. 21, 2013   (GB) .................................. 1311124.0

(51) Int. Cl.
*A61B 6/00*    (2006.01)
*A61B 8/00*    (2006.01)
(Continued)

(52) U.S. Cl.
CPC .............. *A61B 6/502* (2013.01); *A61B 6/025* (2013.01); *A61B 6/0414* (2013.01); *A61B 6/488* (2013.01);
(Continued)

(58) Field of Classification Search
CPC ....... A61B 6/025; A61B 6/0414; A61B 6/488; A61B 6/502; A61B 6/5247; A61B 8/0825;
(Continued)

(56) References Cited

U.S. PATENT DOCUMENTS 3,480,002 A    11/1969   Flaherty et al.
3,964,296 A     6/1976   Matzuk
(Continued)

FOREIGN PATENT DOCUMENTS

DE    19837259       3/2000
DE    19901730 A     7/2000
(Continued)

OTHER PUBLICATIONS

Co-Pending Application No. EP 2577279, File History dated Sep. 2, 2015, 87 pages.
(Continued)

*Primary Examiner* — Ruth S Smith
(74) *Attorney, Agent, or Firm* — New River Valley IP Law, PC; Michele L. Mayberry (57) ABSTRACT

A scanning assembly for a dual-modality automated biological tissue imaging device having first and second compression surfaces is provided. The assembly comprises a housing defining a scanning/compression surface, an ultrasonic transducer mounted within the housing adjacent the scanning surface for movement in a plane parallel to the scanning surface and imaging the tissue through the scanning surface, an X-ray detector mounted within the housing for forming an X-ray image of the tissue based on X-ray radiation passed through the tissue and scanning surface from an X-ray source, and a drive for moving the transducer across the scanning surface so that the transducer generates a plurality of two-dimensional ultrasound tissue images. The housing is hermetically sealed and filled with non-conductive fluid with acoustic impedance resembling that of the tissue. The scanning surface has acoustic impedance resembling that of the tissue and can substantially withstand compression forces applied to the tissue.

11 Claims, 8 Drawing Sheets

(51) Int. Cl.
*A61B 8/08* (2006.01)
*A61B 6/02* (2006.01)
*A61B 6/04* (2006.01)

(52) U.S. Cl.
CPC ............ *A61B 8/0825* (2013.01); *A61B 8/403* (2013.01); *A61B 8/4281* (2013.01); *A61B 8/4416* (2013.01); *A61B 6/5247* (2013.01); *A61B 8/483* (2013.01); *A61B 8/5261* (2013.01); *Y10T 29/49002* (2015.01)

(58) Field of Classification Search
CPC ..... A61B 8/403; A61B 8/4281; A61B 8/4416; A61B 8/483; A61B 8/5261; Y10T 29/49002
See application file for complete search history.

(56) References Cited

U.S. PATENT DOCUMENTS

| | | | |
|---|---|---|---|
| 4,130,112 A | 12/1978 | Frazer | |
| 4,432,371 A | 2/1984 | Mcausland | |
| 4,433,690 A | 2/1984 | Green et al. | |
| 4,567,895 A | 2/1986 | Putzke | |
| 5,303,281 A | 4/1994 | Koller et al. | |
| 5,474,072 A | 12/1995 | Shmulewitz | |
| 5,479,927 A | 1/1996 | Shmulewitz | |
| 5,640,956 A | 6/1997 | Getzinger et al. | |
| 5,664,573 A | 9/1997 | Shmulewitz | |
| 5,872,828 A | 2/1999 | Niklason et al. | |
| 5,938,613 A | 8/1999 | Shmulewitz | |
| 5,983,123 A | 11/1999 | Shmulewitz | |
| 6,036,646 A * | 3/2000 | Barthe | A61B 8/00 128/916 |
| 6,574,499 B1 | 6/2003 | Dines et al. | |
| 6,682,484 B1 | 1/2004 | Entrekin et al. | |
| 6,846,289 B2 | 1/2005 | Besson et al. | |
| 6,876,879 B2 | 4/2005 | Dines et al. | |
| 6,971,991 B2 | 12/2005 | Lasser et al. | |
| 7,264,592 B2 | 9/2007 | Shehada | |
| 7,313,259 B2 | 12/2007 | Alyassin et al. | |
| 7,496,398 B2 | 2/2009 | Nields et al. | |
| 7,739,912 B2 | 6/2010 | Schneider et al. | |
| 7,831,015 B2 | 11/2010 | Li et al. | |
| 7,916,918 B2 | 3/2011 | Suri et al. | |
| 7,940,890 B1 | 5/2011 | Linev | |
| 8,206,307 B2 | 6/2012 | Barnard et al. | |
| 8,323,201 B2 | 12/2012 | Towfiq et al. | |
| 8,325,877 B2 | 12/2012 | Abenaim | |
| 8,326,006 B2 | 12/2012 | Suri et al. | |
| 8,376,946 B2 | 2/2013 | Littrup et al. | |
| 2002/0071523 A1 * | 6/2002 | Busse | A61B 6/035 378/199 |
| 2003/0149364 A1 | 8/2003 | Kapur et al. | |
| 2005/0226371 A1 * | 10/2005 | Kautzer | A61B 6/025 378/37 |
| 2005/0288581 A1 | 12/2005 | Kapur et al. | |
| 2006/0074287 A1 | 4/2006 | Neumann et al. | |
| 2006/0241423 A1 | 10/2006 | Anderson et al. | |
| 2007/0055159 A1 | 3/2007 | Wang et al. | |
| 2007/0263768 A1 | 11/2007 | Ullberg et al. | |
| 2008/0234578 A1 | 9/2008 | Claus | |
| 2008/0242979 A1 | 10/2008 | Fisher et al. | |
| 2008/0255452 A1 | 10/2008 | Entrekin | |
| 2010/0256490 A1 | 10/2010 | Makin et al. | |
| 2011/0224551 A1 | 9/2011 | Barnard et al. | |
| 2012/0190979 A1 * | 7/2012 | McKenna | A61B 5/05 600/431 |
| 2012/0245463 A1 | 9/2012 | Mertelmeier | |
| 2013/0037251 A1 * | 2/2013 | Joshi | G05D 23/1919 165/201 |

FOREIGN PATENT DOCUMENTS

| | | |
|---|---|---|
| EP | 0730431 B1 | 3/2000 |
| GB | 2025617 A | 1/1980 |
| JP | 2008173291 | 7/2008 |
| WO | 0009014 A | 2/2000 |
| WO | 2004030523 A2 | 4/2004 |
| WO | 2004107960 A | 12/2004 |
| WO | 2006015296 A2 | 2/2006 |
| WO | 2008144274 A | 11/2008 |
| WO | 2011153555 A | 12/2011 |
| WO | 2014097231 A2 | 6/2014 |

OTHER PUBLICATIONS

Co-Pending Application No. GB 1311124.0, File History with Office Actions, Responses, Grant Decision, and Issued Patent, dated Sep. 2, 2015, 322 pages.
Co-Pending U.S. Appl. No. 13/642,065, File History, dated Sep. 2, 2015, 206 pages.
Co-Pending International Application No. PCT/IB2013/061174 filed Dec. 20, 2013 (Published as WO 2014/097231 on Jun. 26, 2014).
Co-Pending International Application No. PCT/IB2013/061174, International Preliminary Report on Patentability, dated Jun. 23, 2015, 11 pages.
Co-Pending International Application No. PCT/IB2013/061174, International Search Report and Written Opinion dated Jun. 30, 2014, 15 pages.
Co-pending Application No. PCT/IB2013/061174, International Search Report dated Jun. 30, 2014, 5 pages.
Booi RC, Krücker JF, Goodsitt MM, O'Donnell M, Kapur A, LeCarpentier GL, Roubidoux MA, Fowlkes JB, Carson PL, "Evaluating thin compression paddles for mammographically compatible ultrasound", Ultrasound in Medicine and Biology, 33(3): 462-482, 2007.
Co-Pending Application No. GB 1311124.0, Combined Search and Examination Report, dated Aug. 22, 2013, 10 pages.
Goodsitt MM, Chan HP, Hadjiiski L, LeCarpentier GL, Carson PL, "Automated registration of volumes of interest for a combined x-ray tomosynthesis and ultrasound breast imaging system", Digital Mammography, EA Krupinski (Editor), Lecture Notes in Computer Science 5116, Springer-Verlag, Berlin, pp. 463-468, 2008.
Irving BJ, Maree GJ, Hering ER, Douglas TS, "Radiation dose from a linear slit scanning x-ray machine with full-body imaging capabilities", Radiation Protection Dosimetry, 130(4): 482-489, 2008.
Novak D, "Indications for and comparative diagnostic value of combined ultrasound and X-ray mammography", European Journal of Radiology, 3(Supplement 1): 299-302, 1983.
Sinha SP, Roubidoux MA, Helvie MA, Nees AV, Goodsitt MM, LeCarpentier GL, Fowlkes JB, Chalek CL, Carson PL, "Multi-modality 3D breast imaging with X-ray tomosynthesis and automated ultrasound", Proceedings of the 29th International Conference of the IEEE EMBS, Lyon, France, pp. 1335-1338, Aug. 23-26, 2007.
Suri JS, Danielson T, Guo Y, Janer R, "Fischer's fused full field digital mammography and ultrasound system (FFDMUS)", Medical and Care Compunetics 2, edited by L Bos, IOS Press, pp. 177-200, 2005.
Tesic MM, Piccaro MF, Munier B, "Full field digital mammography scanner", European Journal of Radiology, 31: 2-17, 1999.

* cited by examiner

DUAL-MODALITY MAMMOGRAPHY

CROSS-REFERENCE TO RELATED APPLICATIONS

The present application relies on the disclosure of and claims priority to and the benefit of the filing date of South African Application No. ZA201209726 filed on Dec. 21, 2012, and U.K. Application No. GB1311124.0 filed on Jun. 21, 2013, the disclosures of which are hereby incorporated by reference herein in their entireties.

BACKGROUND OF THE INVENTION

Field of the Invention

This invention relates to an apparatus and method for imaging human tissue which use geometrically registered X-ray and ultrasound imaging techniques. In particular, the invention relates to improvements to existing dual-modality mammography equipment which uses a combination of such techniques, as well as to apparatus for augmenting and improving conventional mammography equipment.

Description of the Related Art

Dual-modality imaging systems that use a combination of full-field digital mammography and automated breast ultrasound imaging in a single device are known. These devices combine the benefits of both imaging techniques to obtain more effective and accurate diagnosis of carcinoma or other abnormalities in particularly breast tissue.

The applicant's international patent application number WO2011/153555 entitled "DUAL-MODALITY SCANNING SYSTEM FOR DETECTING BREAST CANCER" discloses such a dual-modality scanning apparatus that incorporates both X-ray and ultrasound technologies. The apparatus at least partially alleviates a number of problems experienced with other previously known dual-modality apparatus and meets five specific functional attributes including: (1) that the breast is in the same orientation and degree of compression when X-ray and ultrasound images are obtained; (2) that both sets of images are acquired simultaneously so as to minimize the time the patient's breast is held stationary and compressed between the compression plates; (3) that automated breast ultrasound images of the whole breast are acquired in a single scan; (4) that both image modalities are acquired in three dimensions (3D); and (5) that radiation dose exposure to the patient is minimized.

To achieve these functional attributes the apparatus comprises an X-ray source arranged to generate an output beam having a reference axis; a pre-collimator arranged to modify the output beam to generate a fan beam; a platform defining a first surface for supporting a breast of a patient; a first drive arranged to move the pre-collimator transverse to the reference axis, thereby to impart motion to the fan beam; a linear scanning element comprising an X-ray sensor and an ultrasound transducer supported adjacent to and beneath the first surface and extending parallel to the fan beam and reference axis; a second drive arranged to move the linear scanning element transverse to the reference axis, in synchronisation with the first drive, while both x-ray and ultrasound scanning are being conducted, thereby to generate a two-dimensional X-ray image and a three-dimensional ultrasound image of the breast; a third drive arranged to rotate the X-ray source relative to the platform, thereby to generate a plurality of sets of two-dimensional X-ray images of the breast for tomosynthesis purposes; and a processor for implementing tomosynthesis reconstruction algorithms to generate three-dimensional X-ray and ultrasound images, and to co-register the three-dimensional X-ray and ultrasound images.

In use, the tissue to be scanned, typically a breast, is compressed between the first surface and a compression plate which is mechanically lowered onto the breast so as to effect the compression in order to pull as much of the breast tissue from the chest wall as possible and spread the breast tissue out across the platform to a uniform thickness. This compression separates out overlying breast structures and improves image clarity obtained by the X-ray and ultrasound scanners. In addition, the more the breast tissue can be compressed, the lower the X-ray dosage will be that is required to conduct effective X-ray scanning. However, due to the discomfort generally associated during significant compression of the breast tissue, excessive compression is not desirable.

WO2011/153555 is incorporated herein, in its entirety, by reference.

In the apparatus described in WO2011/153555 as well as other known dual-modality scanning devices, the automated ultrasound transducer is generally mounted below or above one of the compression surfaces, as the case may be, which in turn are substantially in direct contact with the breast being scanned while simultaneously immobilising the breast and maintaining uniform compression thickness of the breast tissue. To avoid contact and possible damage caused by contact between the X-ray detector or ultrasound transducer and compression surface below or above which it is mounted during scanning, the X-ray detector and ultrasound transducer are generally mounted slightly removed from the compression surface. A disadvantage of this configuration is that it necessitates the impending X-ray radiation and ultrasonic waves to move through regions of air before reaching the X-ray detector, compression platform or ultrasound transducer, as the case may be. This results in impedance mismatches and acoustic reflection of the ultrasonic waves at the compression platform interface, which in turn negatively affects the ultrasound images obtained, as well as potential X-ray signal attenuation and geometric blurring due to the finite X-ray focal point. As compression of the breast can also result in temporary deformation of the compression surface, the distance at which the X-ray detector and ultrasound transducer have to be mounted from the compression surface has to be sufficient to accommodate the deformation while avoiding contact with the scanning surface during scanning.

In addition to the impedance mismatch at the compression platform interface, the problem for the ultrasound imaging is exacerbated at the outermost extremities (most distal parts) of the breast between the compression surfaces. At these distal portions, the natural curvature of the breast creates spaces which act as air barriers between the breast tissue and the compression surfaces to the generally perpendicular ultrasound beams emitted by the linear transducer on the opposite side of one of the compression surfaces. This results in a peripheral volume of the breast not being accessible, or being poorly accessible, to the ultrasound beams, yielding inferior imaging of the breast in these regions. To alleviate this problem the ultrasound beams need to be steered appropriately into the peripheral volume of the breast.

Despite previous efforts in developing imaging systems, including those described in U.S. Pat. Nos. 8,325,877; 7,313,259; 6,846,289; 6,574,499; 6,876,879; 6,682,484; 3,480,002; 4,433,690; 6,971,991; 7,831,015; 8,376,946; 7,496,398; 5,872,828; 4,567,895; 7,739,912; 5,474,072; 5,479,927; 7,916,918; 8,326,006; 8,323,201; 8,206,307;

5,640,956; 5,303,281; 7,940,890; 4,432,371; 7,264,592; 5,474,072; 5,479,927; 5,664,573; 5,938,613; 5,983,123; 3,964,296; 4,130,112; and U.S. Application Publication Nos. 20080234578; 20080242979; 20030149364; 20050288581; 20120245463; 20070055159; 20110224551; 20060241423; 20080255452; 20100256490; 20060074287; 20070263768; International Application Publication Nos. WO2008144274, WO00/09014, WO2004030523, WO2004107960, WO2006015296, WO2011153555; European Patent No. 0730431; UK Patent Application No. GB2025617; German Patent Application No. DE19901730A1; German Patent No. DE 29914663 U1, as well as those described in various non-patent literature (See Booi et al., Evaluating Thin Compression Paddles For Mammographically Compatible Ultrasound, Ultrasound in Med. & Biol., Vol. 33, No. 3, pp. 472-482, 2007; Goodsitt et al., Automated Registration of Volumes of Interest for a Combined X-Ray Tomosynthesis and Ultrasound Breast Imaging System, Lecture Notes in Computer Science Volume 5116, 2008, pp 463-468; Irving et al., Radiation Dose From A Linear Slit Scanning X-Ray Machine With Full-Body Imaging Capabilities Radiation Protection Dosimetry (2008), Vol. 130, No. 4, pp. 482-489; Novak, Indications for and Comparative Diagnostic Value of Combined Ultrasound and X-Ray Mammography, Europ. J. Radiol. 3 (1983) 299-302; Sinha et al., Multi-modality 3D breast imaging with X-Ray tomosynthesis and automated ultrasound, Proceedings of the 29$^{th}$ Annual International Conference of the IEEE EMBS Cite Internationale, Lyon, France, Aug. 23-26, 2007; Suri et al., Fischer's Fused Full Field Digital Mammography and Ultrasound System (FFDMUS)), Medical and Care Compunetics 2, p 177-200, 2005; and Tesic et al., Full field digital mammography scanner, European Journal of Radiology 31 (1997) 2-17), each of which is hereby incorporated by reference herein in its entirety, there is still a need for improvements to existing dual-modality scanning apparatus which will at least partially alleviate the problems mentioned above.

SUMMARY OF THE INVENTION

Embodiments of the invention provide a scanning assembly for an automated biological tissue imaging device, such as a dual-modality imaging device, of the type having first and second compression surfaces adapted for compressing and immobilising the biological tissue therebetween, the system comprising:

a housing defining a scanning surface which acts as one of the first and second compression surfaces;

an ultrasonic transducer mounted within the housing adjacent to the scanning surface for movement in a plane parallel to the scanning surface and imaging the tissue through the scanning surface; and a drive configured to move the transducer in a predetermined path across the scanning surface during imaging so that the transducer generates a plurality of two-dimensional ultrasound images of the tissue; the assembly being characterised in that the housing is hermetically sealed and is filled with a non-conductive fluid with an acoustic impedance resembling that of the tissue, the scanning surface has an acoustic impedance resembling that of the tissue and material properties enabling it to withstand compression forces applied to the tissue without substantial deformation, and in that the housing includes sealed electrical connectors for connecting the ultrasound transducer and drive to control circuitry of the tissue imaging device.

Further features of embodiments of the invention provide for the non-conductive fluid to have a specific acoustic impedance of about 1.3 MRayl; for the non-conductive fluid to be an oil, such as mineral oil; and for the hermetically sealed housing to contain substantially no water or air.

Still further features of embodiments of the invention provide for the tissue imaging device to be a dual-modality mammography system incorporating both X-ray and ultrasound imaging techniques for imaging the biological tissue, which includes an X-ray detector mounted within the housing adjacent to the scanning surface, the X-ray detector being configured to form an X-ray image based on X-ray radiation passed through the biological tissue and scanning surface from an X-ray source, and for the electrical connector to be further adapted to connect the X-ray detector to control circuitry of the mammography system; for the X-ray detector to be a linear slot X-ray detector; for the ultrasound transducer to be an elongate, linear transducer; and for the X-ray detector and ultrasound transducer to be mounted to the drive in side-by-side configuration to form a combined scanning element capable of acquiring both X-ray and ultrasound images simultaneously and linearly across the scanning surface.

Additional features of embodiments of the invention include a dual-modality mammography system wherein the combined scanning element is mounted to a drive along rails, and the non-conductive fluid completely immerses the scanning element, drive, and rails such that the ultrasound transducer is configured to move right up against an inner surface of the scanning surface during use. In embodiments, the non-conductive fluid remains at a constant volume within the housing when the drive is engaged to move the scanning element such that the pressure of the non-conductive fluid against the scanning surface provides constant support underneath the scanning surface against compressive forces at the top of the scanning surface. Still additional embodiments of the invention may include a dual-modality mammography system with no fluid in the housing of the system such that only air covers the scanning element, drive, and rails, or a system comprising a combination of various fluids, such as air and oil.

Yet further features of embodiments of the invention provide for the scanning assembly to include an optical laser surface scanner, which optical laser surface scanner can optionally be mounted within the housing, the optical laser surface scanner being configured to scan a peripheral surface of a peripheral volume of the biological tissue being imaged and to collect data about the surface area of the peripheral volume, the data being useful for dynamically steering an ultrasound beam of the ultrasound transducer into the peripheral volume during scanning in; for the optical laser surface scanner to be optionally mounted to the drive to form a combined scanning element with the X-ray detector and ultrasound transducer; for the optical laser surface scanner to be optionally mounted for movement with the ultrasonic transducer; alternatively for it to be mounted to a separate drive within the housing which is configured to move it in a path across the scanning surface; for the laser scanner to be optionally mounted to the combined scanning element with the X-ray detector and ultrasound transducer; for the X-ray detector to be, in embodiments, a flat panel detector mounted adjacent and parallel to the scanning surface; for the ultrasound transducer to be optionally mounted to the drive between the flat panel X-ray detector and scanning surface and to be configured to conduct ultrasound imaging of the biological tissue before or after X-ray imaging and to be entirely retreated from above the X-ray detector while X-ray imaging is being conducted so as not to interfere with the X-ray imaging.

A further feature of embodiments of the invention provides for the ultrasound transducer to be a slimline linear ultrasound transducer with a laterally attached electronic ribbon cable.

Further features of embodiments of the invention provide for the tissue imaging device to be configured to utilise an ultrasonic pre-scan to establish a biological tissue volume dataset representing the biological tissue and utilise the tissue volume dataset to determine a measure of the biological tissue density which, in turn, is used to determine an appropriate X-ray exposure for use during X-ray imaging of the tissue; and to include a processor for implementing digital breast tomosynthesis reconstruction algorithms to generate three-dimensional X-ray and ultrasound images from two-dimensional X-ray and ultrasound images of the tissue taken with the ultrasound transducer and X-ray detector. Digital breast tomosynthesis reconstruction algorithms include Filtered Back Projection (FBP), Simultaneous Algebraic Reconstruction Technique (SART), Maximum Likelihood Expectation Maximization (MLEP), and others (See Reiser et al., Comparison of reconstruction algorithms for digital breast tomosynthesis, The 9th International Meeting on Fully Three-Dimensional Image Reconstruction in Radiology and Nuclear Medicine Jul. 9-13, 2007, Lindau, Germany, http://arxiv.org/abs/0908.2610). Embodiments of the invention include a set of computer-executable instructions for executing the digital breast tomosynthesis reconstruction algorithms stored in a form of computer-readable memory which may include random-access memory (RAM) or read-only memory (ROM). Computer-executable instructions can be embedded in computer hardware or stored in the computer-readable memory such that the processor may be directed to perform the reconstruction algorithms.

Further embodiments of the invention provide a method of manufacturing a scanning assembly for a biological tissue imaging device, such as a dual-modality imaging device, used for imaging biological tissue of the type having first and second compression surfaces adapted for compressing and immobilising the biological tissue therebetween, comprising the steps of:

mounting a scanning assembly including at least an ultrasonic transducer to a drive within a housing and adjacent to a scanning surface defined by the housing for movement on the drive in a plane parallel to the scanning surface and imaging of the tissue through the scanning surface;

providing an electrical connector on a surface of the housing for connecting the ultrasound transducer and drive to control circuitry of the biological tissue imaging device;

filling the housing with a non-conductive fluid with an acoustic impedance resembling that of the tissue, completely immersing the scanning assembly and drive in the fluid;

bleeding and drying the filled housing so as to remove substantially all air and water from the housing; and hermetically sealing the housing, thus ensuring that the fluid is kept at a constant volume during use.

Still further embodiments of the invention provide a method of setting the X-ray exposure in a dual-modality mammography system used for imaging biological tissue comprising the steps of gathering a volume data set representing the biological tissue by means of an ultrasound pre-scan utilising an ultrasound transducer of the system; determining a measure of density of the biological tissue using the volume data set; and setting the X-ray exposure according to the measure of density of the biological tissue.

Yet further embodiments of the invention provide a method of enabling a reduction in compression of a breast between first and second compression surfaces adapted for compressing and immobilising the breast therebetween, in a dual-modality mammography system incorporating both X-ray and ultrasound imaging techniques for imaging the breast, comprising the steps of:

mounting a three-dimensional ultrasound transducer and a linear slot X-ray detector to a drive in side-by-side configuration within a housing defining a scanning surface which acts as one of the compression surfaces, to form a combined scanning assembly capable of acquiring both X-ray and ultrasound images simultaneously and linearly across the scanning surface;

filling the housing with a non-conductive fluid with an acoustic impedance resembling that of the breast, completely immersing the scanning assembly and drive in the fluid; and using the scanning assembly inside the filled housing to obtain ultrasound and X-ray images of a breast located between the scanning surface and a second compression surface.

Still further embodiments of the invention provide a method of enabling a reduction in a dose of X-ray radiation utilised in a dual-modality mammography system incorporating both X-ray and ultrasound imaging techniques for imaging a breast, comprising the steps of:

mounting an ultrasound transducer and a linear slot X-ray detector to a drive in side-by-side configuration within a housing defining a scanning surface which acts as one of two compression surfaces between which the breast is compressed, to form a combined scanning assembly capable of acquiring both X-ray and ultrasound images simultaneously and linearly across the scanning surface;

filling the housing with a non-conductive fluid with an acoustic impedance resembling that of the breast, completely immersing the scanning assembly and drive in the fluid; and using the scanning assembly inside the filled housing to obtain ultrasound and X-ray images of a breast located between the scanning surface and a second compression surface.

These and other features of the invention will be described in more detail in the description of certain embodiments of the invention that follows.

BRIEF DESCRIPTION OF THE DRAWINGS

The accompanying drawings illustrate certain aspects of some of the embodiments of the present invention, and should not be used to limit or define the invention. Together with the written description, the drawings serve to explain certain principles of embodiments of the invention.

DETAILED DESCRIPTION OF VARIOUS EMBODIMENTS OF THE INVENTION

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

Figure 1:
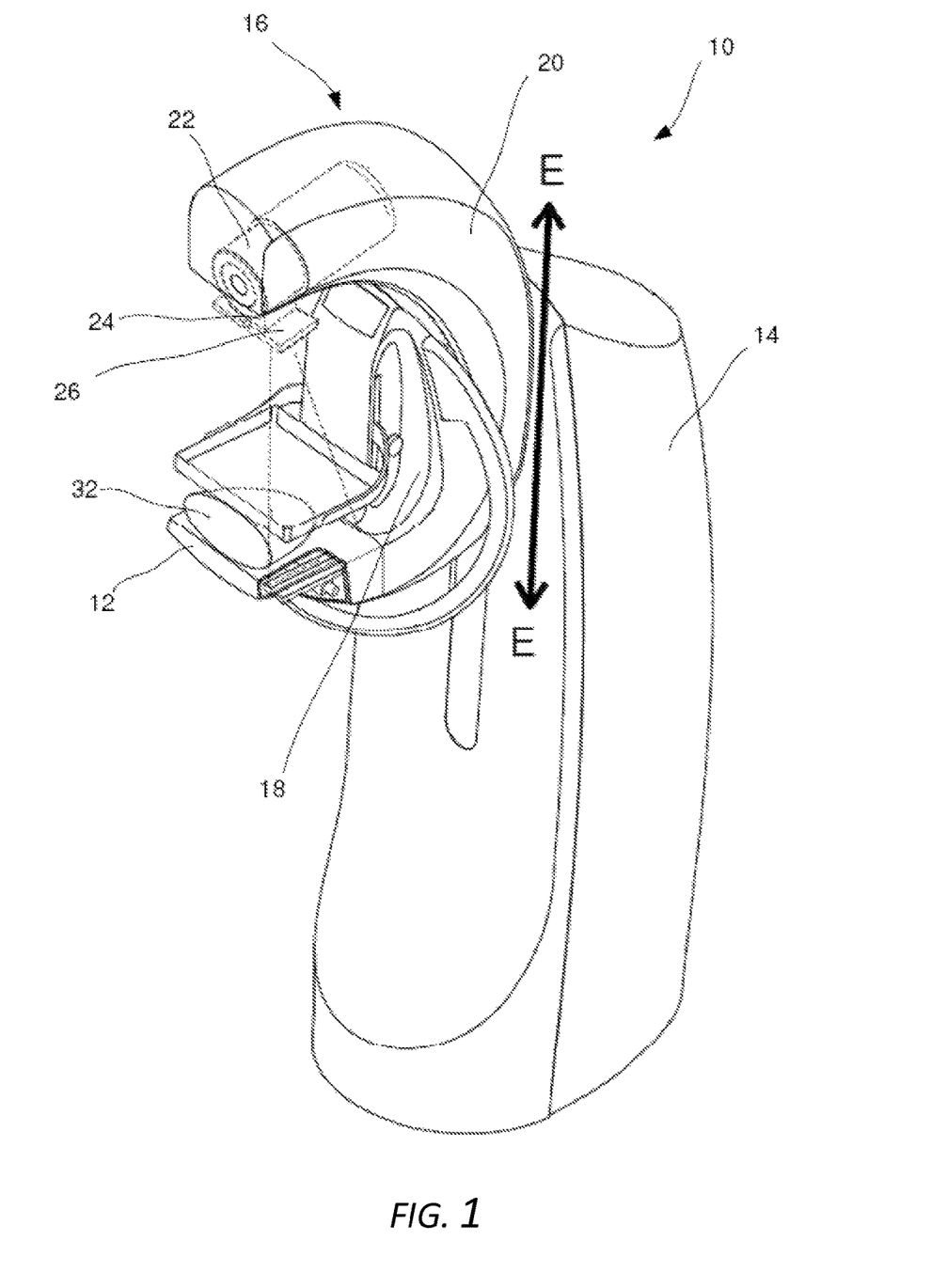
FIG. 1 is a schematic diagram providing a representation of a dual-modality mammography system utilising a scanning assembly in accordance with an embodiment the invention.

In accordance with one embodiment of the invention, a dual-modality mammography system (10) utilising a scanning assembly (12) is shown in FIG. 1. The system (10) may include a support pillar (14) on which is mounted a C-arm (16). The C-arm (16) may include a base member (18), which is rotatably mounted to the support pillar (14), and an overhanging arm (20) mounted so as to be rotatable relative to both the base member (18) and the support pillar (14). The arm (20) may include an X-ray source (22) with an X-ray beam-shaper (24) and pre-collimator (26).

The C-arm (16) may be adjustable in its entirety in a direction parallel to the support pillar (14), indicated in FIG. 1 by arrows (E), and can be rotated about its attachment point to the support pillar (14) by means of appropriate drive mechanisms (not shown).

Figure 2:
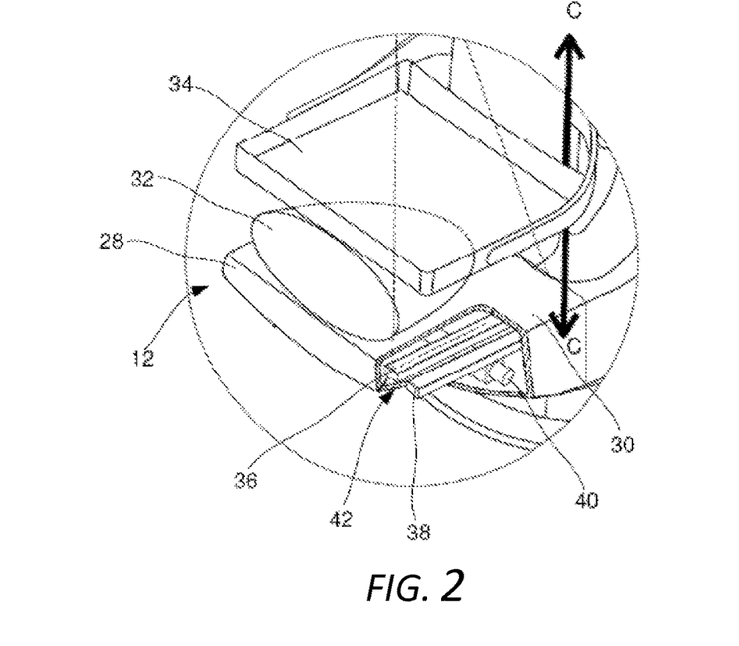
FIG. 2 is a schematic diagram providing an exploded view of a part-sectional representation of the scanning assembly of the dual-modality mammography system of FIG. 1.

The scanning assembly (12), shown in more detail in the embodiment shown in FIG. 2, may include a housing (28) which defines a scanning surface (30) which also acts as a support surface on which a breast (32) of a human patient, or any other biological matter, can be placed. The scanning surface (30) may also act as a first compression surface which cooperates with a second compression surface provided by a compression plate (34). The compression plate (34) may be mounted for independent movement towards and away from the scanning surface (30) so as to compress and immobilise the breast (32) between it and scanning surface (30). Alternatively, in other embodiments the compression plate (34) may be fixed and the vertical position of housing (28) may be adjustable such that scanning surface (30) is capable of movement towards or away from the compression plate (34). This movement of either the compression plate (34) or housing (28) or both may be achieved by means of a linear drive mechanism (not shown). The dimensions of the scanning surface (30) and compression plate (34) can be chosen so as to accommodate the largest breast to be measured. This allows positioning of the patient's breast over a distal edge of the scanning surface (30), thereby enabling the compression plate (34) to draw the patient's axilla tissue into the scanners field of view. This ensures that the tissue in the patient's axillary breast region can be fully imaged. In addition, the scanning surface may comprise an acoustic coupling fluid placed on top of the surface during use to facilitate transmission of ultrasound between the surface and breast tissue. The acoustic coupling fluid may be any liquid or gel, such as oil, which allows ultrasound to pass through.

It may also be appreciated that the C-arm assembly (16) may be positioned in an inverse configuration such that overhanging arm (20) may be positioned toward the bottom of the support pillar (14) (such that arm (20) is underhanging) and the scanning surface (30) may be positioned toward the top of the support pillar (14). This configuration would result in the X-ray source (22) with an X-ray beam-shaper (24) and pre-collimator (26) pointed upward (instead of downward as shown) toward the scanning surface (30), which would point downward. It is within the capability of a skilled artisan to make such a configuration operable in light of this disclosure.

Figure 8:
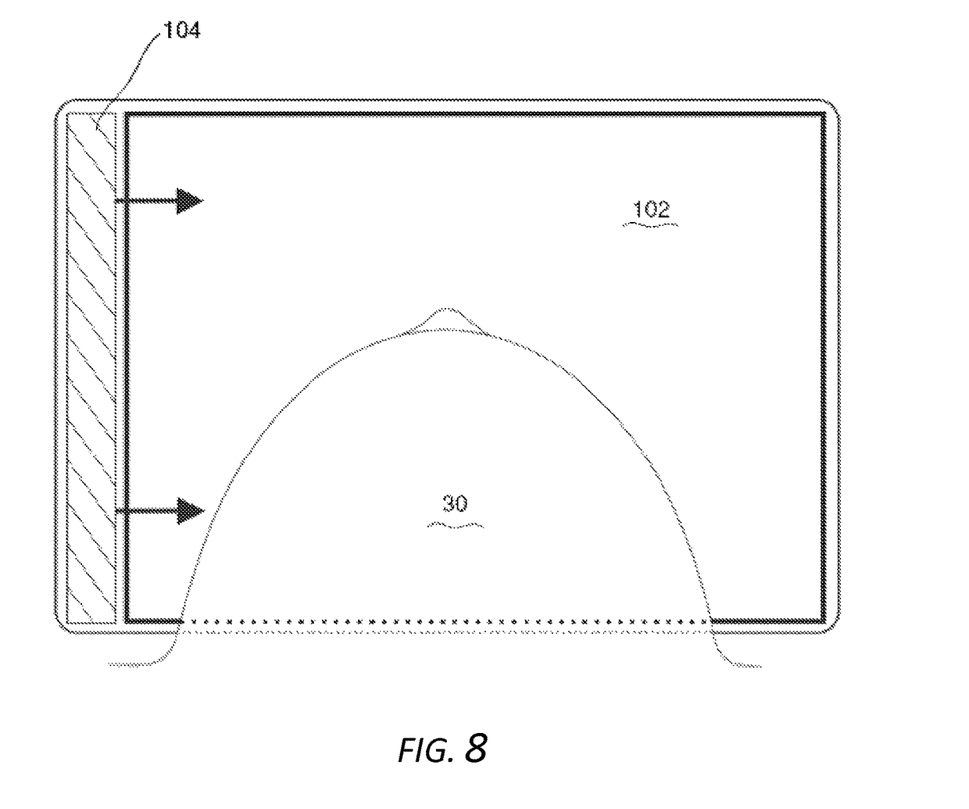
FIG. 8 is a schematic diagram providing a top plan view representation showing the operation of a scanning assembly in accordance with the embodiment of the invention shown in FIG. 7.
Figure 9:
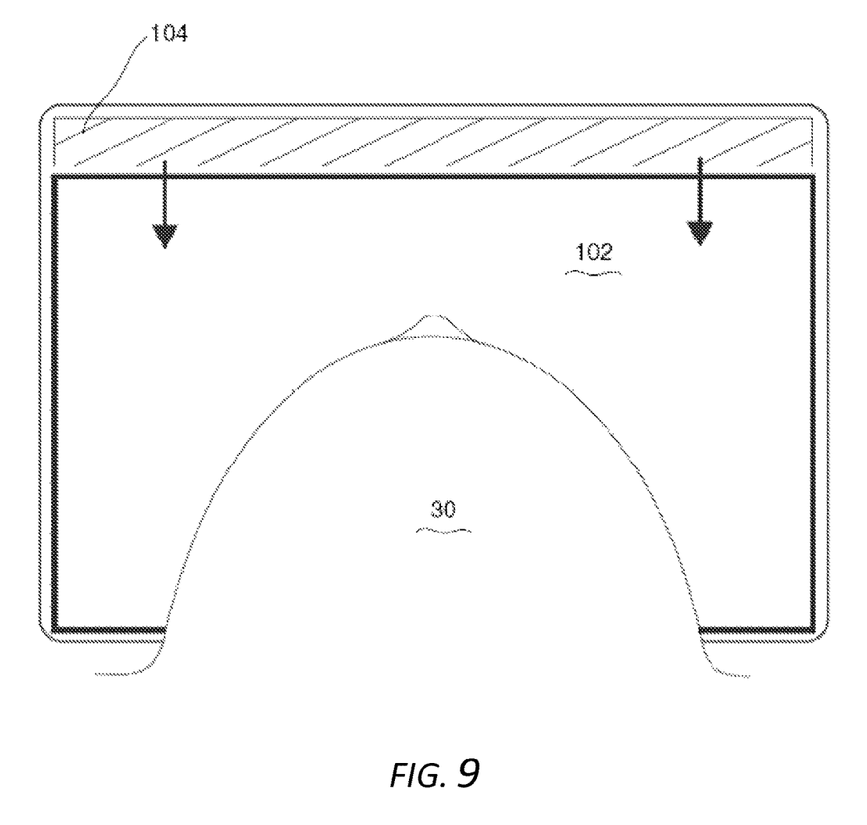
FIG. 9 is a schematic diagram providing a top plan view representation showing the operation of the scanning assembly of FIG. 7 in an alternative configuration.

The scanning assembly (12) may further include a linear slot X-ray detector (36) and an ultrasound transducer (38) which can be mounted on a pair of rails (40) inside the housing (28). The rails (40) are mounted to facilitate transverse movement of the X-ray detector (36) and ultrasound transducer (38) in a plane parallel to the scanning surface (30) and parallel to a plane defined by the transverse movement of the X-ray source (22). Linear slot X-ray detector (36) and ultrasound transducer (38) together define a dual-modality linear scanning element (42) which enables simultaneous acquisition of X-ray and ultrasound images of the breast tissue compressed between the scanning surface (30) and compression plate (34). The scanning element (42) may be moved along the rails (40) by means of a linear drive means (not shown) also mounted within the housing (28). The linear drive means may include any suitable scanning mechanism for moving the scanning element along the rails. Scanning element (42) and rails (40) may be configured to scan along the scanning surface laterally as shown in FIG. 8. However, in other embodiments, the scanning element and rails may be configured to scan along the scanning surface transversely as shown in FIG. 9. Additionally, other embodiments of the scanning assembly may include only one rail, or more than two rails, such as three, four, or even five rails or more for moving the scanning element.

Figure 3:
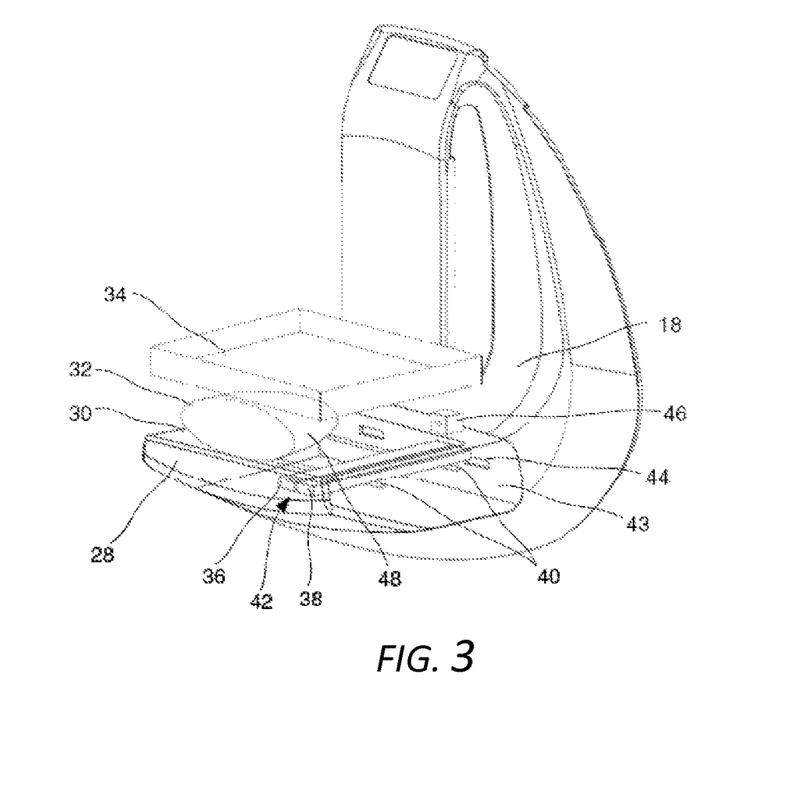
FIG. 3 is a schematic diagram providing a representation of a first embodiment of a scanning assembly in accordance with the invention.
Figure 4:
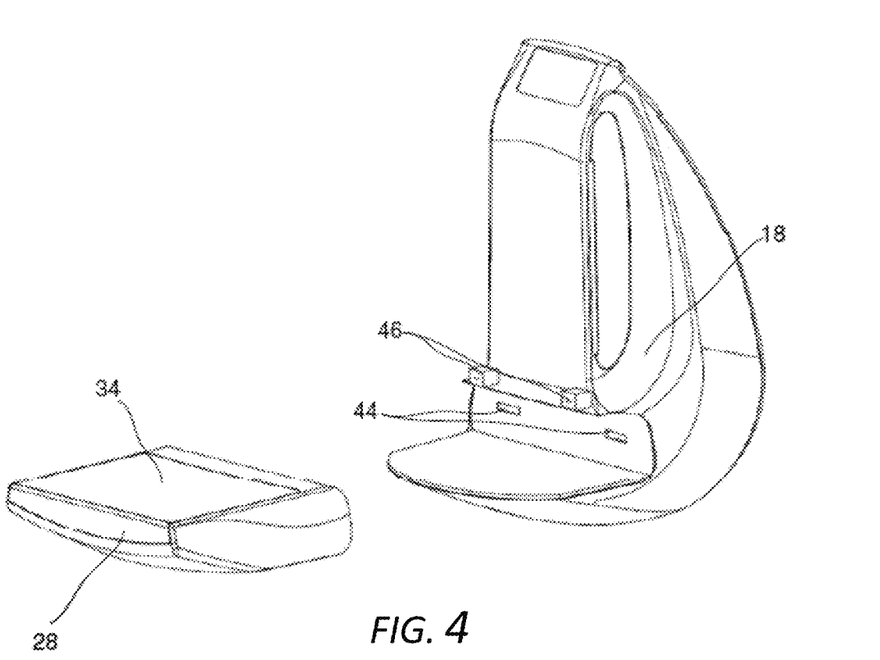
FIG. 4 is a schematic diagram providing a representation illustrating the detachability of a scanning assembly of FIG. 3.

In embodiments, the housing (28) including scanning element (42) and its associated drive are provided as a standalone unit which is manufactured separately and is removably attachable to the base member (18), as shown in more detail in FIGS. 3 and 4. The interior region (43) of the housing (28) may be entirely filled with a non-conductive fluid (e.g. oil) with an acoustic impedance corresponding to that of fatty tissue such as is present in breast tissue, thus completely immersing the scanning element (42), rails (40) and drive mechanism in the oil (as used herein, the term "non-conductive fluid" is intended to mean a fluid with a dielectric constant equal to or less than 3). The filling of housing (28) with oil is conducted during a bleeding and drying process which removes substantially all air and water from the housing (28), after which housing (28) is hermetically sealed, thus ensuring that the fluid is kept at a constant volume during use.

The scanning surface of the scanning assembly may be manufactured from a material which will be able to withstand the compression forces exerted on it by the compressed breast tissue. These forces may be as high as 200N acting over a minimum surface area of 100 mm². It has been found that polymethylpentene (PMP), a thermoplastic polymer of methylpentene monomer units, better known commercially by its trade name "TPX®" (Mitsui Chemicals America, Inc, Rye Brook, N.Y.) exhibits adequate material strength properties to warrant its use to manufacture the surface of the housing which acts as the scanning surface. In addition, TPX® also has suitable acoustic impedance properties to warrant its use in the scanning assembly as well as superior clarity and transparency. However, other thermoplastic polymers with similar properties may be used.

It is desirable that the scanning surface resist significant deformation under the compressive forces. The larger the deformation of the scanning surface, the further the X-ray detector and ultrasound transducer have to be placed from the scanning surface. This results in a reduction in imaging performance. By keeping the non-conductive fluid (e.g., mineral oil) at a constant volume during compression, the fluid acts to support the TPX® surface, thereby preventing significant deformation.

In order to achieve adequate acoustic coupling between the transducer, the scanning surface and the breast tissue, the ultrasound probe may be acoustically coupled with suitable liquids and/or solids and, unlike in the case of existing systems, not air. The non-conductive fluid in the housing achieves this acoustic coupling and may effectively act as an interface between the underside of the TPX® scanning surface, which is static, and the top of the ultrasound probe which is translating. In addition, it is desired that the scanning surface acoustically match both the ultrasonic transducer and the breast tissue. In addition to its compressive properties, TPX® was found to be a suitable material to achieve adequate acoustic coupling.

Figure 5:
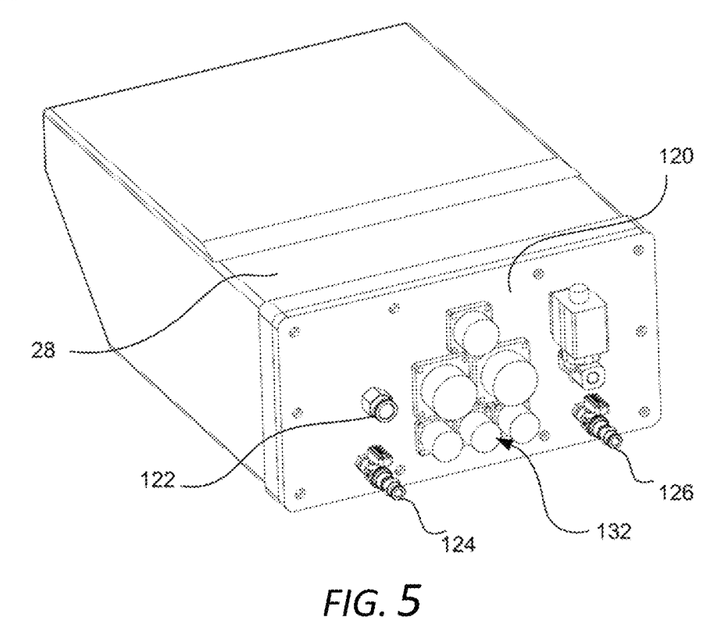
FIG. 5 is a schematic diagram providing a representation illustrating the back of a scanning assembly showing connectors used during bleeding and drying of the assembly.
Figure 6:
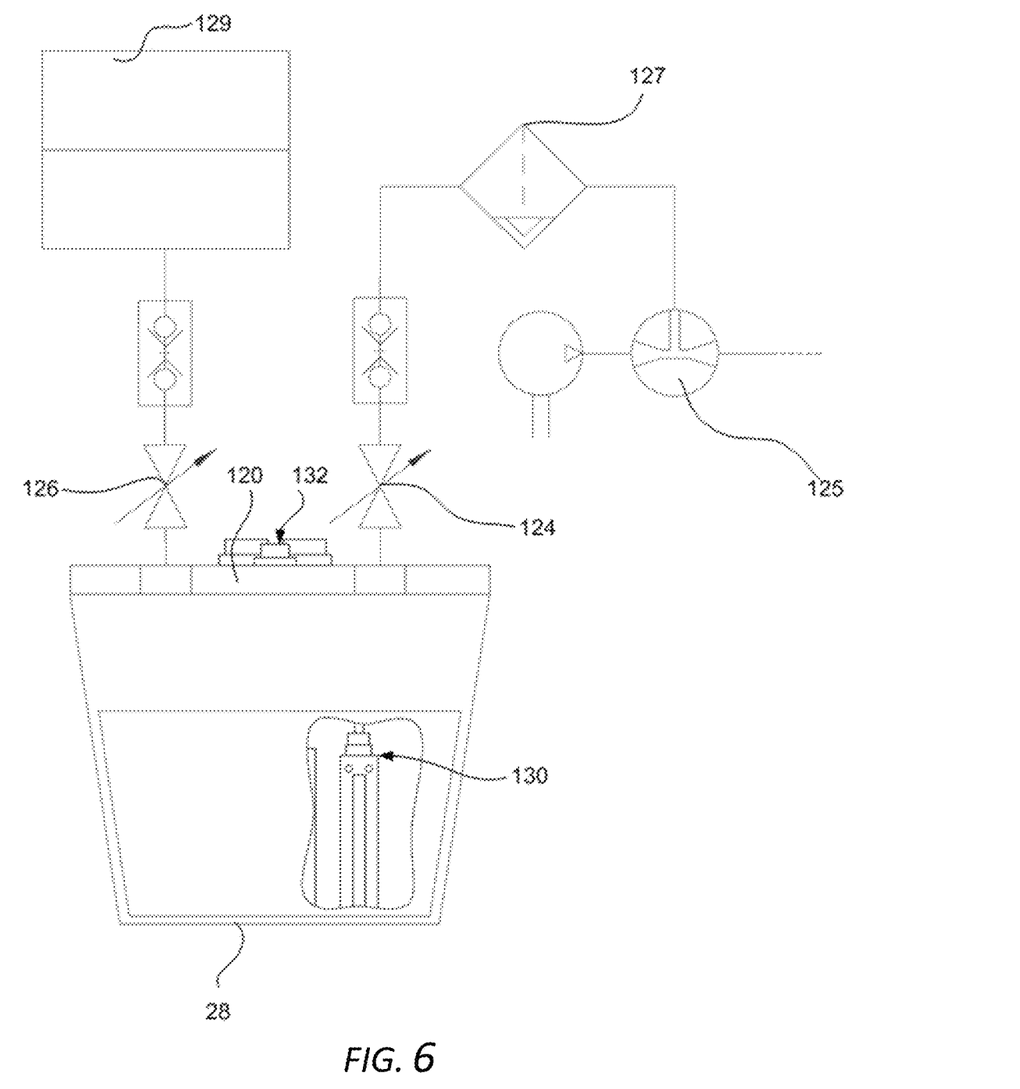
FIG. 6 is a schematic diagram providing a flow diagram illustrating the bleeding and drying process of the scanning assembly.

It is desirable that no air bubbles are present inside the scanning assembly housing, as these would disrupt the acoustic coupling and show up as imperfections on the ultrasound and X-ray images. With reference to FIGS. 5 and 6, and as mentioned above, the filling of the housing (28) with non-conductive fluid may be achieved through a bleeding and drying process which removes substantially all air and water from the housing. To do so, the back plate (120) of the housing (28) includes one fluid-carrying connector (122) and two bleeding connectors (124, 126). The fluid-carrying connector (122) may be used for gross filling of the housing (28). The bleeding of the housing may be conducted as follows:

1. With both connectors (124, 126) shut off and the back plate (120) in an upward orientation, a low pressure is applied to the first bleeding connector (124) and an oil reservoir (129) is connected to the second bleeding connector (126).

2. The first connector (124) is then opened and a low pressure applied to the housing, which is created by a venturi (125) which is connected via a low pressure container (127) to the first connector (124). This causes the volume of internal bubbles in the housing (28) to increase resulting in increased buoyancy. The bubbles will then rise quickly to the upper surface of the housing (28).

3. The second connector (126) is then opened slightly to allow oil to replace the volume of the bubbles which are sucked out of the first connector (124).

4. It is envisaged that by vibrating the housing (28), micro bubbles may be encouraged to move towards the first connector.

5. Once all the bubbles have been removed, both connectors (124, 126) are closed and locked.

As an alternative to the above bleeding procedure, the entire housing may be bled in a vacuum.

The housing may also include an electrical connector (130) for connecting electronic control circuitry of the X-ray detector (36), ultrasonic transducer (38) and drive to control circuitry of the mammography system (10). It should be appreciated that the control circuitry can be terminated in a male electrical plug (132) provided on an operatively rear surface of the housing (28) which is attachable to complementary female sockets (44) provided on the base member (18) or vice versa.

The beam shaper (24) may be configured to generate a cone-shaped beam of X-rays that diverges outwardly towards the scanning surface (30), with a diameter sufficient to ensure coverage of the breast (32) to be imaged. The cone beam has a central upright reference axis that is normal to the plane defined by the scanning surface (30) and the planes in which the X-ray source and the linear scanning element (42) move. Typically, the cone-shaped beam has a cone angle of approximately 30 degrees. The pre-collimator (24) may define a slot which, when placed in the path of the X-ray beam, generates a generally planar fan beam which is narrowest adjacent to the pre-collimator (24) and broadens in the direction of the scanning surface (30). The pre-collimator (24) can be moved in a plane parallel to the breast support surface (30) so that a number of fan beams, each having a different inclination relative to the upright reference axis of the cone-shaped X-ray beam, can be generated, according to the orientation of the pre-collimator slot. Thus, each fan beam may be at a different pre-determined angle relative to the reference axis of the cone-shaped X-ray beam.

The pre-collimator (24) can be arranged to be indexed between predetermined positions, but may be driven continuously between desired positions which are selected according to the number of fan beams required and the size of the breast to be scanned. The scanning assembly (12) may also include a post-collimator (not shown) located between the scanning surface (30) of the housing (28) and the X-ray detector (36). The post-collimator will typically comprise a layer of lead sandwiched between layers of aluminium and has slots with a width calculated to eliminate any penumbra from the impinging fan beams, typically having a width of about 4 mm for a pre-collimator slot width of 0.4 mm.

It will be appreciated that, as with prior art systems, arm (20), to which the X-ray source (22) is attached can be decoupled from the base member (18), and rotated so as to allow a plurality of X-ray images to be taken of the breast (32) from different angles. The resulting multiple two-dimensional images can be used to generate a three-dimensional X-ray image of the breast using an appropriate digital breast tomosynthesis ("DBT") algorithm.

The linear scanning element used in the prototype embodiment of the apparatus was a CCD based detector with an active imaging area of 8,520×242 pixels where each pixel is 27×27 microns. This, in conjunction with a fan beam of 3 to 5 millimeters width, permits operation of the CCD detector in a Time Delay and Integration (TDI) mode which provides superior sensitivity and lower noise, enabling the use of a lower X-ray dose than would otherwise be required. It is expected that a CMOS detector will allow faster data clocking and consequently a higher scan speed of approximately 150 mm/second compared to the CCD detector.

The pre-collimator (24) optionally has an associated linear axis drive (not shown) which adjusts the position of the pre-collimator slot in order to generate an X-ray fan beam at the required angle. The compressor plate (34) may have an associated linear axis drive, and the X-ray detector (36) and ultrasound transducer (38) may have an associated linear axis drive that moves the X-ray detector (36) and the ultrasound transducer (38) transversely within the housing (28) below, just below scanning surface (30). Further, in some embodiments, the linear axis drive may be configured to move the X-ray detector (36) and ultrasound transducer (38) through multiple passes, either laterally or transversely, along the scanning surface during use, such as through two passes, three passes, four passes, or more.

In embodiments, the C-arm (16) has two associated drives, a rotational axis drive which permits rotation of the C-arm in relation to the support pillar (14), and a vertical axis drive which allows adjustment of the vertical position of the C-arm (16) on the pillar (14). High precision linear position encoders associated with the pre-collimator and the X-ray slot detector drives provide the alignment control position data required for the fan beam to be incident on the X-ray slot detectors imaging element. The apparatus may be assembled in such a way that the linear guides of the X-ray source (22), pre-collimator (24) and X-ray slot detector (36) linear axes are precisely parallel and the X-ray slot detector (36) itself is precisely parallel to the fan beam (that is, orthogonal to its linear axis). The X-ray source or tube (22) may be powered by a high frequency generator that is controlled by an image acquisition and scanning controller. The controller may also control the respective linear axis drives, and the rotational and vertical C-arm drives. The controller may in turn be connected to a human machine interface, typically a computer terminal, with an associated 3D image display unit or other devices, such as a printer, a storage device, or computer network. The X-ray detector (36) may have associated readout electronics integrated with it, and the ultrasound transducer (38) may have associated electronics integrated with it, both of which feed raw data to an image reconstruction processor.

In use, prior to an imaging examination, the C-arm (16) may be rotated about its axis of rotation on the support pillar (14) to the desired angle, between 0 and 180 degrees, and driven to the correct vertical height on the support pillar (14) to match the patient's breast height. The three linear axes of the respective drives on the C-arm (16) for the pre-collimator (24), the compression plate (34), and the scanning element (42), respectively, may then be synchronized and all moved to their respective home positions.

The patient's breast (32) may then be placed on the scanning surface (30) of the scanning assembly (12) and the compression plate (34) may be activated to provide a preliminary compressive pressure, to immobilize the breast and pull breast tissue away from the chest wall. A start signal may then be issued via the human machine interface to initiate a breast scan. An additional compressive force may then be applied by the drive of the compressor plate (34). The X-ray source (22) may be energized by the high frequency generator, with a preliminary exposure technique (kV & mA) based on the breast thickness, determined from the compression plate's linear position, to generate an X-ray cone beam which may be pre-collimated by the pre-collimator (24) and filtered by the X-ray filter to produce a filtered X-ray fan beam.

Tight collimation (0.4 mm) near the source minimizes the back scatter to the patient when compared with collimation techniques applied on top of the breast. In an embodiment with an X-ray source focal spot size of 0.3 mm and a source to detector distance of 650 mm, cone beam collimation using a slot with a width of 0.4 mm results in a primary fan beam width of approximately 4 mm incident on the X-ray detector (36), which has an active width of 6 mm. This provides significantly greater X-ray flux and better tube loading characteristics when compared with slit scanning configurations that collimate to the width of single pixel detectors<0.1 mm wide.

The pre-collimator (24) may move in synchronization with the X-ray detector (36) to cause the X-ray fan beam to move across the breast at a linear velocity of up to 150 mm/s. The relative positioning of the X-ray source (22), the pre-collimator (24), and the X-ray detector (36) to achieve correct beam alignment may be performed according to the calibration data acquired from an automatic beam alignment process. The filtered X-ray fan beam is attenuated and scattered by the breast. The X-ray fan beam post-collimator collimates the X-ray photon flux exiting the breast to eliminate the scattered photons and ensure that only the primary photons impinge on the X-ray slot detector (36).

In some embodiments, the multi row linear slot X-ray detector (36) operates in Time Delay and Integration (TDI) mode and the detector readout line clock may be electronically synchronized with the detector linear axis velocity. The detector may accumulate charge across each row of pixels in the imaging element to provide a single image line to an analogue-to-digital convertor in the readout electronics. Digitized line data may be compiled into a two-dimensional image projection during the scan by the image reconstruction processor.

In some embodiments, the linear ultrasound transducer (38), together with its associated control electronics, generates two-dimensional images for each position of the transducer across the scanning surface (30). Because the ultrasound transducer (38) moves in synchrony with the X-ray detector (36) along the pair of guide rails (40), it is able to capture multiple 2D images which, when fed into the image reconstruction processor, generates 3D ultrasound images of the breast (32). The processor is also able to co-register the 2D X-ray image with the 3D ultrasound image, thus aiding in the diagnosis of underlying pathology.

The apparatus can also be used to gather multiple 2D X-ray images of the breast. This is accomplished by rotating the X-ray tube (22) by means of the angular axis drive, and repeating the X-ray image acquisition sequence described above. The multiple 2D images can then be sent to the image reconstruction processor which then implements a DBT algorithm to generate 3D X-ray images of the breast. These 3D X-ray images can be co-registered with the 3D ultrasound images to improve diagnosis.

The embodiment of the invention described above has a number of advantages over prior art systems. In particular, it should be apparent that the presence of the non-conductive fluid, such as an oil, for example, mineral oil, in the housing (28) of the scanning assembly (12) allows the ultrasound scanner to move right up against an inner surface of the scanning surface (28), as it provides superior lubrication properties compared to the air that is present in conventional scanning apparatus. This makes it possible for the ultrasound transducer to achieve substantially the same breast tissue imaging coverage as the X-ray detector which would be very difficult to accomplish otherwise. In addition, the volume of non-conductive fluid, such as oil, inside the housing allows the ultrasound transducer to be laterally abutted against the X-ray detector in a side-by-side configuration. This ensures optimal lateral breast tissue imaging coverage on either side of the scanning surface. Due to the hermetically sealed nature of the housing and the fact that it is substantially free from air or water, the housing is substantially less compressible than it would have been had it not been for the presence of the oil. The incompressibility of the housing allows both the X-ray detector and ultrasound transducer to scan very close or even adjacent to the underside of the scanning surface and, accordingly, the breast tissue, which minimises X-ray signal attenuation that may be caused by the non-conductive fluid, e.g., oil, and the geometric blurring due to the finite X-ray focal spot, as well as the X-ray radiation dose required.

Mineral oil has an acoustic impedance of about 1.3 MRayl, which is very close to that of the fatty tissue found in the breast, and may be used in certain embodiments of the invention. As used herein, when the term "about" precedes a particular value, it is intended to describe a range within 10% below to 10% above that particular value. Mineral oil also has a relatively low dielectric constant (approximately 2.1 at room temperature) and therefore very low electrical conductivity and can consequently be used as insulation oil in electrical environments. It also has better heat dissipating properties than air and therefore has superior cooling capabilities. By immersing the complete scanning element, drive and electrical connections in mineral oil within the housing, the ultrasound transducer is acoustically matched to the compressed breast tissue above the platform, while the assembly electronics continue to function normally and are effectively cooled. While mineral oil is one oil that may be used in the housing, it should be appreciated that other suitable fluids with similar properties may be used, which may include other petroleum-based oils, fluorinated hydrocarbon-based oils, silicone oil, and vegetable oils. For example, a list of materials and their dielectric constants is provided at http://www.rafoeg.de/20,Dokumentenarchiv/20,Daten/dielectric_chart.pdf.

In the embodiment of the invention shown in FIGS. 3 and 4, the scanning assembly (10) also includes two optical laser surface scanners (46) mounted adjacent to the scanning surface (30) of the scanning assembly (12). The laser surface scanners are optionally configured to scan a peripheral surface (48) of the breast (32) positioned between the scanning surface (30) and the compression plate (34). The scanning may be conducted during a normal image acquisition scan. The data collected by the laser surface scanners (46) may then be used by the ultrasound beam-former electronics to dynamically steer the ultrasound beam produced by the ultrasound transducer (38) into the peripheral volume of the breast so as to obtain optimal ultrasound imaging of the breast (32). It will be appreciated that the laser surface scanners (46) could improve the quality of ultrasound images obtained at the peripheral portions of the tissue being scanned and at least partially alleviate the problems experienced by conventional scanning apparatus in this regard. It is also envisaged that the laser surface scanners may be mounted with the X-ray detector (36) and ultrasound transducer (38) and may be configured to move with the scanning element (42) or independently by means of their own drive.

Figure 7:
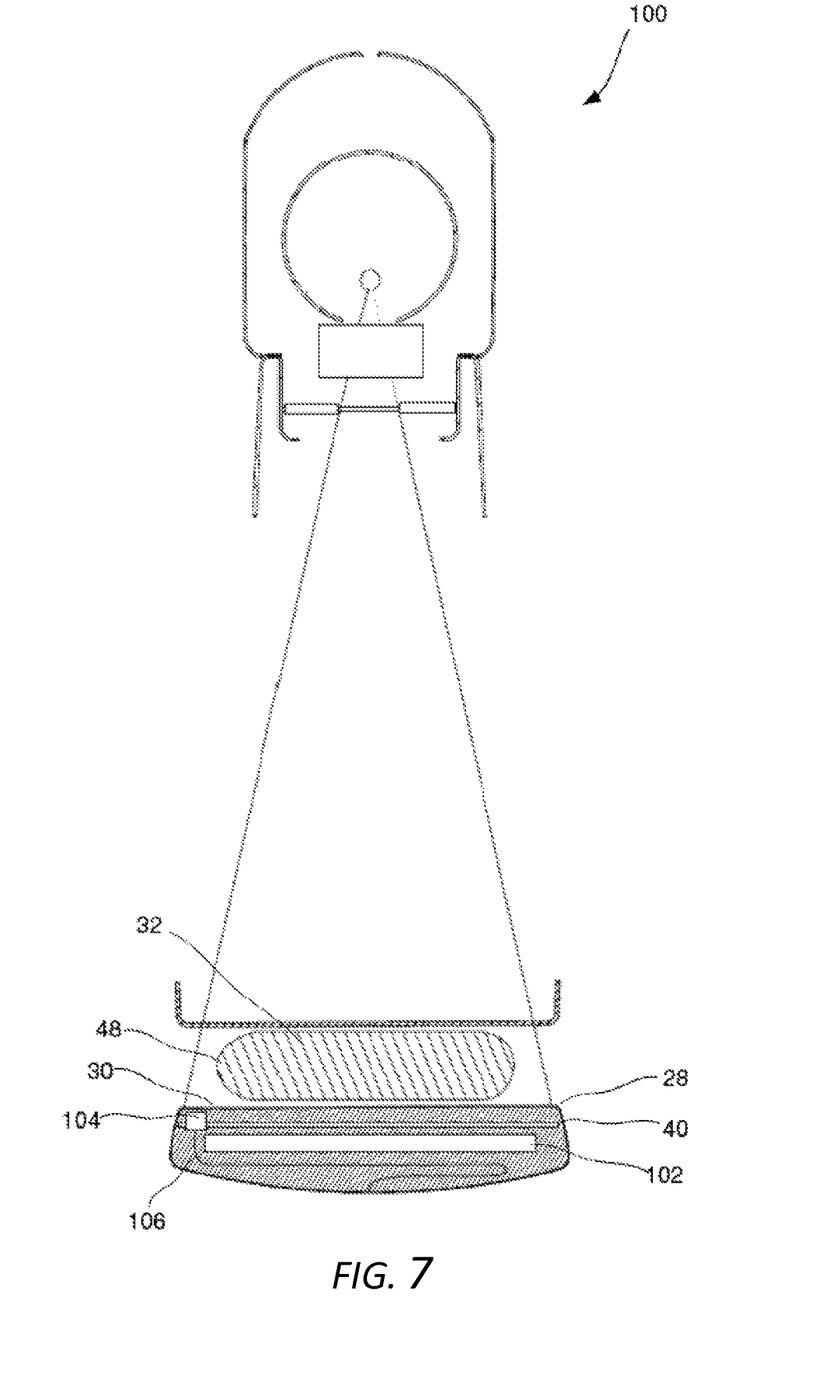
FIG. 7 is a schematic diagram providing a sectional front elevation view representation of a dual-modality mammography system utilising a scanning assembly in accordance with a second embodiment of the invention.

Further, the modular construction of the scanning assembly according to embodiments of the invention also lends the scanning assembly to be used to improve existing scanning systems and apparatus. In these cases, the scanning assembly may be retrofitted to the existing apparatus, thereby providing the benefits of the invention without the need to replace the entire apparatus. This will provide access to the improved scanning abilities of a scanning assembly according to embodiments of the invention at a greatly reduced cost. An embodiment of one such system (100) is shown in FIG. 7. In the figure, like elements to those described with reference to FIGS. 1 to 4 are indicated with like reference numerals. The system (100) is of the type that acquires X-ray images using a flat panel detector (102). The flat panel detector (102) is incorporated inside the oil-filled housing (28), below the guide rails (40) on which an ultrasound transducer (104) is mounted. The ultrasound transducer (104) is a linear, generally elongate (commonly referred to in the art as "slimline") transducer with a laterally attached ribbon cable (106) and is positioned between the flat panel detector (102) and scanning surface (30). Ultrasound transducer (104) can be configured to scan across the underside of the scanning surface (30) after the X-ray full field exposure and the associated X-ray grid has been retracted to obtain the ultrasound volume imaging data of the compressed breast (32).

As before, the housing (28) of the scanning assembly (12) may be completely filled with oil, such as mineral oil, thereby providing the benefits described in more detail above. The flat panel X-ray detector (102) and ultrasound transducer (104), as well as the drive mechanism for the ultrasound transducer and all the associated electrical connections may again be submerged in the oil within the housing (28). It should also be appreciated that the ultrasound transducer (104) may be mounted for movement laterally across the scanning surface as shown in FIG. 8, or transversely as shown in FIG. 9. It is envisaged that the scanning assembly of this embodiment of the invention may be retrofitted to existing flat panel X-ray detector based systems with minimal modification of the existing system.

It is also envisaged that a scanning assembly according to embodiments of the invention may be used to add ultrasound scanning capabilities to existing X-ray only scanning systems. In such an embodiment one of the compression surfaces of the system may be replaced with an oil-filled scanning assembly as described above which contains only an ultrasound transducer. In this way ultrasound capabilities may be added to the X-ray only systems.

It is furthermore envisaged that the ultrasound transducer in any of the embodiments of the invention described above, may be configured to scan over the scanning surface before X-ray scanning to acquire a scout scan volume dataset of the breast being imaged, which can be used to determine a measure of the breast density and use this to set the most appropriate X-ray settings for the forthcoming X-ray exposure. This provides an effective method of automatic exposure control which does not use ionizing radiation, and which can reduce the amount of radiation to which the breast or other tissue being scanned is ultimately exposed to. Existing techniques use an X-ray pre-exposure to assess the breast density which increases the radiation dose absorbed by the tissue.

Figure 10:
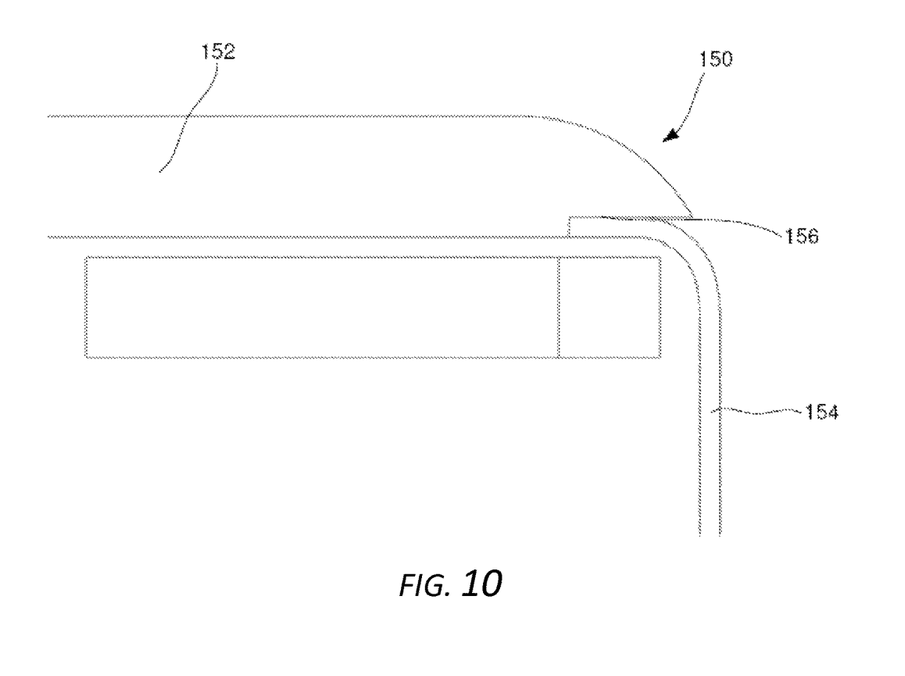
FIG. 10 is a schematic diagram providing a representation illustrating a section of the front edge of a scanning assembly according to an embodiment of the invention.

In an embodiment of the invention, the edges of the scanning assembly which will be in contact with the patient can have a radius of no less than 5 mm. FIG. 10 shows a section of the front edge (150) of the scanning assembly, showing the geometry of a TPX® (152)—carbon fibre reinforced polymer (CFRP) (154) glued bond (156).

In order to control the pressure inside and the volume of the scanning assembly, volume of the fluid in the assembly must be kept constant during compression to provide support for the TPX® platform. As mentioned before, the housing, in particular the scanning surface, must be rigid and not deflect under compression. To achieve this, the housing may be constructed from rigid CFRP. This allows for a thin (e.g. 0.1 to 2.0 mm, such as 0.5 mm) front edge which does not flex under compression. As described above, the housing as also hermetically sealed so as to prevent the escape of fluid and the ingress of fluid or air. The TPX® scanning surface and CFRP housing may be made according to various manufacturing techniques known in the art, including 3D printing, extrusion, extrusion blow molding, injection molding, blow molding, and pultrusion.

When there is no compression on the scanning surface or the assembly is being transported in the cargo section of an airplane, the fluid may be allowed to flow in and out of the housing to prevent the build-up of pressure due to external pressure and temperature changes. To achieve this, the assembly may be fitted with a normally open solenoid valve and bladder during transport. The valve may be closed during use or simply while there is compression on the scanning surface.

The hermetic sealing of the unit can be achieved by taking, among others, the following measures:

1. At the TPX®-CFRP bond (156) a special glue may be used to mechanically bond the surfaces. More ductile epoxy can be used to waterproof this bond. Alternatively, the TPX® platform may be attached to the CFRP housing using an O-ring seal and stitching, with the stitches providing compression between the platform and the housing.

2. An O-ring seal (not shown) may be used on the back plate (120) of the assembly. This seal allows for mechanical loads to be transferred from the CFRP to the back plate. This also prevents flexion of the "open" end (120) of the assembly.

3. The electrical connectors fitted to the back plate can be waterproof rated multi-pole connectors. These allow electrical power and signals to be transmitted in and out of the box while ensuring oil/air is unable to leak through the electrical wiring. These power/signal lines can be used to power the drive on the rails as well as the scanning assembly which preferably includes the ultrasound transducer and x-ray detector.

Compression of the breast tissue in conventional mammography systems is necessary for a variety of reasons including amongst others: to reduce the thickness of the breast to improve the image quality by reducing the amount of scattered radiation produced, to reduce the required radiation dose and to fixate the breast and thus avoid motion blur. It has, however, been found that if the compressive load on the breast tissue is significantly reduced, for example from 95 N to 54 N, that there is also a marked reduction in the amount of discomfort and pain experienced by the patient. For this reason it is desirable to not only reduce the compressive force applied to the breast tissue, but also the amount of compression of the breast tissue. In embodiments, compressive loads achieved during use may be in the ranges of 20 N to 200 N, such as 50 N to 190 N, or 75 N to 150 N, or for example from 90 N to 180 N, or 30 N to 70 N, or 35 N to 65 N, or such as from 35 N to 70 N, 40 N to 60 N, 45 N to 60 N, or 45 N to 55 N, or any range in between.

On the other hand, insufficient compression of the breast tissue could mean that the images obtained by the ultrasound imaging are not clear, as the ultrasound transducer generally has a finite depth to which it can effectively image into the breast tissue. In addition, the thickness to which the breast tissue to be imaged has been compressed, generally has a direct correlation to the amount of radiation that is required to obtain images of sufficient quality and resolution.

It has been found that the use of the hermetically sealed, liquid filled scanning assembly of embodiments of the invention, which allows both the X-ray and ultrasound probes to operate closer to the scanning surface, in particular in combination with the use of the linear slot X-ray detector, allows adequate imaging to be done while compressing the breast to a lesser extent and also using a lower dose of radiation. In particular it has been found that use of the assembly and method of embodiments of the invention enable a reduction in breast compression of up to 50%, such as for example from 100N to 50N, 110N to 50N, 110N to 40N, and 90N to 50N, less breast compression, such as for example 60 mm instead of 40 mm, or 70 mm instead of 50 mm and a reduction in radiation dose of up to 50%, such as for example from between 3 and 4 mGy to 1.5-2.0 mGy. This is made possible by, amongst others, the fact that the slot-scanning X-ray detector has inherently less scatter than traditional flat panel X-ray detectors and also has a higher signal to noise ratio which translates into better image quality. In addition, the 3D ultrasound transducer used in the device according to embodiments of the invention has the ability to operate to a depth of up the 80 mm, which caters for the majority of breast thicknesses encountered in practice.

The above description is by way of example only and it will be appreciated that numerous changes and modifications may be made to the embodiments described without departing from the scope of the invention. Further, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. It should be evident that the particular illustrative embodiments disclosed above may be altered or modified and all such variations are considered within the scope and spirit of the present invention.

While systems and methods are described in terms of "comprising," "having," "containing," or "including" various components or steps, the systems and methods can also "consist essentially of" or "consist of" one or more of the various components or steps. All numbers and ranges disclosed in this specification may vary by some amount. Whenever a numerical range with a lower limit and an upper limit is disclosed, any number and any included range falling within the range is specifically disclosed. In particular, every range of values disclosed herein is to be understood to set forth every number and range encompassed within the broader range of values. Moreover, the indefinite articles "a" or "an," as used in the claims, are defined herein to mean one, at least one, or more than one of the element it introduces. All references cited in this specification, including patents, patent applications, non-patent literature publications, etc., are hereby incorporated by reference herein in their entireties. If there is any conflict in the usages of a word or term in this specification and one or more patent or other documents cited herein, the definitions consistent with this specification should be adopted.

The invention claimed is:

1. A scanning assembly for a dual-modality automated biological tissue imaging device having first and second compression surfaces for compressing and immobilising the biological tissue therebetween, the assembly comprising:

a housing defining a scanning surface which acts as one of the first and second compression surfaces;

an ultrasonic transducer mounted within the housing for movement in a plane parallel to the scanning surface and imaging the biological tissue through the scanning surface; and an X-ray detector mounted within the housing for forming an X-ray image of the tissue based on X-ray radiation passed through the biological tissue and the scanning surface from an X-ray source;

wherein the housing is hermetically sealed and is filled with a non-conductive liquid which completely immerses the ultrasonic transducer and the X-ray detector such that liquid is present between the scanning surface and the X-ray detector and X-ray radiation is passed through the liquid when forming the X-ray image;

the scanning surface has material properties enabling it to withstand compression forces applied to the biological tissue without substantial deformation;

and the housing comprises sealed electrical connectors for connecting the ultrasound transducer and the X-ray detector to control circuitry of the tissue imaging device.

2. The scanning assembly of claim 1 comprising a drive within the housing for moving the ultrasonic transducer and the X-ray detector, or only the ultrasonic transducer, in a predetermined path across the scanning surface during imaging and wherein the housing comprises a sealed electrical connector for connecting the drive to control circuitry of the tissue imaging device.

3. The scanning assembly of claim 1 wherein the non-conductive liquid has an acoustic impedance of 1.3 MRayl.

4. The scanning assembly of claim 3 wherein the non-conductive liquid is oil based.

5. The scanning assembly of claim 1 wherein the X-ray detector is a linear slot X-ray detector.

6. The scanning assembly of claim 5 wherein the X-ray detector and the ultrasound transducer are mounted to form a combined scanning element for acquiring both X-ray and ultrasound images simultaneously and linearly across the scanning surface.

7. The scanning assembly of claim 1 wherein the ultrasound transducer is an elongate, linear transducer.

8. The scanning assembly of claim 1 wherein the X-ray detector is a flat panel detector mounted parallel to the scanning surface.

9. The scanning assembly of claim 8 wherein the ultrasound transducer is mounted to a drive between the flat panel X-ray detector and the scanning surface and during use the ultrasound transducer conducts ultrasound imaging of the biological tissue before or after X-ray imaging and to be entirely retreated from above the X-ray detector while X-ray imaging is being conducted so as not to interfere with the X-ray imaging.

10. The scanning assembly of claim 9 wherein the ultrasound transducer is an elongate, linear ultrasound transducer with a laterally attached electronic ribbon cable.

11. A method of manufacturing a scanning assembly for a biological tissue imaging device used for imaging biological tissue having first and second compression surfaces for compressing and immobilising the biological tissue therebetween, comprising the steps of:

mounting an ultrasonic transducer to a drive within a housing for movement of the ultrasonic transducer on the drive in a plane parallel to a scanning surface defined by the housing and imaging of the tissue through the scanning surface;

mounting an X-ray detector within the housing for forming an X-ray image of the tissue based on X-ray radiation passed through the tissue and the scanning surface from an X-ray source;

providing an electrical connector on a surface of the housing for connecting the ultrasound transducer, the X-ray detector and the drive to control circuitry of the biological tissue imaging device;

filling the housing with a non-conductive liquid, completely immersing the ultrasonic transducer, the X-ray detector and the drive in the liquid;

bleeding and drying the filled housing so as to remove substantially all air and water from the housing; and hermetically sealing the housing, thus ensuring that the liquid is kept at a constant volume during use.

* * * * *